United States Patent [19]
Rueb et al.

[11] Patent Number: 4,997,472
[45] Date of Patent: Mar. 5, 1991

[54] TETRAHYDROINDAZOLES WITH A PHENYL ETHER STRUCTURE, COMPOSITIONS AND USE

[75] Inventors: Lothar Rueb, Speyer; Karl Eicken, Wachenheim; Peter Plath, Frankenthal; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 457,973

[22] Filed: Dec. 27, 1989

[30] Foreign Application Priority Data

Jan. 20, 1989 [DE] Fed. Rep. of Germany ....... 3901550

[51] Int. Cl.$^5$ .................. A01N 43/56; C07D 405/12
[52] U.S. Cl. ........................................ 71/92; 71/90; 548/369
[58] Field of Search ...................... 548/369; 71/90, 92

[56] References Cited

FOREIGN PATENT DOCUMENTS 0105721  4/1984  European Pat. Off. .

*Primary Examiner*—Robert W. Ramsuer
*Attorney, Agent, or Firm*—Keil & Weinkauf

[57] ABSTRACT

N-(Phenyl)-tetrahydroindazole derivatives of the general formula Ia and Ib

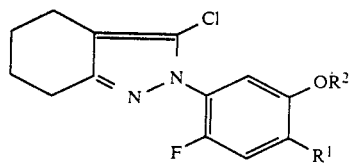

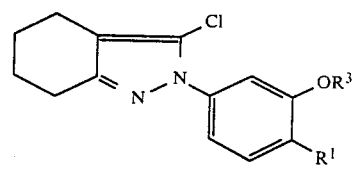

where
$R^1$ is halogen;
$R^2$ is $C_1$–$C_6$-alkoxycarbonyl-$C_3$–$C_5$-alkenyl or $C_1$–$C_3$-alkyl which is substituted in the 1- or 2-position by $C_1$–$C_6$-alkoxycarbonyl or a 5- or 6-membered saturated or monounsaturated heterocycle which contains one oxygen or sulfur as heteroatom and can be substituted by from one to four $C_1$–$C_4$-alkyls, and
$R^3$ is $C_2$–$C_7$-alkyl, $C_3$–$C_6$-alkenyl, $C_3$–$C_6$-alkynyl, $C_1$–$C_6$-alkoxycarbonyl-$C_3$–$C_5$-alkenyl of $C_1$–$C_3$-alkyl which is substituted in the 1- or 2-position by $C_1$–$C_6$-alkoxycarbonyl or a 5- or 6-membered saturated or monounsaturated heterocycle which contains one oxygen or sulfur as heteroatom and can be substituted by from one to four $C_1$–$C_4$-alkyls, their manufacture and their use.

5 Claims, No Drawings

TETRAHYDROINDAZOLES WITH A PHENYL ETHER STRUCTURE, COMPOSITIONS AND USE

The present invention relates to novel N-phenyltetrahydroindazole derivatives of the general formulae Ia and Ib

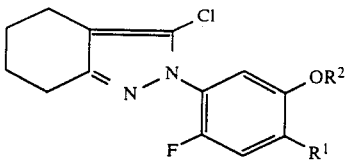

Ia

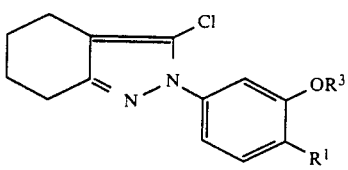

Ib where
$R^1$ is halogen,
$R^2$ is $C_1$-$C_6$-alkoxycarbonyl-$C_3$-$C_5$-alkenyl or $C_1$-$C_3$-alkyl which is substituted in the 1 or 2 position by $C_1$-$C_6$-alkoxycarbonyl or a 5- or 6-membered saturated or monounsaturated heterocycle which contains one oxygen or sulfur as heteroatom and can be substituted by one to four $C_1$-$C_4$-alkyls, and
$R^3$ is $C_2$-$C_7$-alkyl, $C_3$-$C_6$-alkenyl, $C_3$-$C_6$-alkynyl, $C_1$-$C_6$-alkoxycarbonyl-$C_3$-$C_5$-alkenyl or $C_1$-$C_3$-alkyl which is substituted in the 1 or 2 position by $C_1$-$C_6$-alkoxycarbonyl or a 5- or 6-membered saturated or monounsaturated heterocycle which contains one oxygen or sulfur as heteroatom and can be substituted by one to four $C_1$-$C_4$-alkyls.

The present invention also embraces all the stereoisomeric forms of the compounds Ia and Ib.

The present invention additionally relates to the preparation of the compounds Ia and Ib, to the use thereof as herbicides, and to mixtures for controlling undesired plant growth, which contain these compounds Ia and Ib.

The herbicidal action of N-phenyltetrahydroindazoles has been disclosed. Thus, for example, EP-A 105,721 describes derivatives of the formula I'

I' where, inter alia,
Y is chlorine or bromine,
Z is chlorine or methyl and
R is $C_1$-$C_4$-alkyl, $C_3$-$C_4$-alkenyl, $C_3$-$C_4$-alkynyl, $C_1$-$C_6$-alkoxycarbonylmethyl or $C_1$-$C_4$-halogenoalkoxycarbonylmethyl.

However, there is a search for compounds which, with low application rates, have an improved action against undesired plants and are tolerated by crop plants (are selective).

In accordance with this object, we have found the N-phenyltetrahydroindazole derivatives Ia and Ib defined in the introduction. We have also found processes for the preparation of these compounds and the use thereof for the selective control of undesired plant growth.

The N-phenyltetrahydroindazole derivatives Ia and Ib according to the invention can be obtained in a variety of ways.

They are obtained, for example, by an appropriately substituted N-(3-hydroxyphenyl)tetrahydroindazole IIa and IIb being etherified with an appropriate compound IIIa and IIIb in a conventional manner at up to 200° C., preferably at from 25° C. to 150° C., in an inert organic solvent in the presence of a base

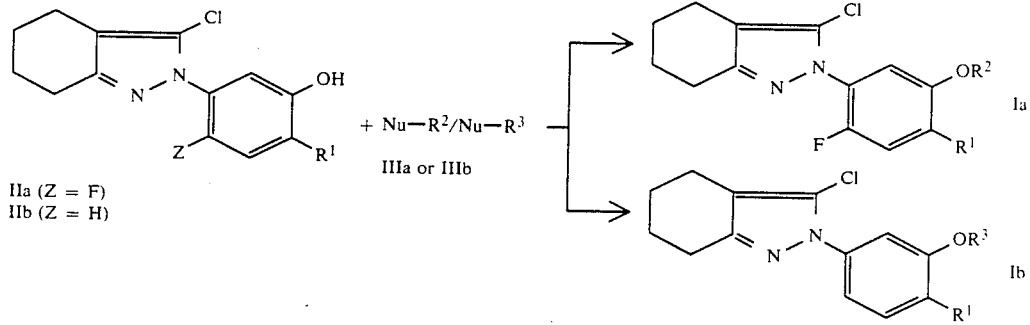

IIa (Z = F)
IIb (Z = H)

In the formulae IIIa and IIIb, Nu is a conventional nucleophilic leaving group such as halogen, e.g. chlorine, bromine and iodine, or sulfonyloxy, e.g. methylsulfonyloxy, trifluoromethylsulfonyloxy, phenylsulfonyloxy and tolylsulfonyloxy. Nu is preferably chlorine, bromine and tolylsulfonyloxy.

Particularly suitable for the reaction are aprotic polar solvents such as acetone, acetonitrile, dimethylformamide, dimethyl sulfoxide, tetrahydropyran and corresponding mixtures.

The reaction is preferably carried out in acetone, acetonitrile and dimethylformamide or corresponding mixtures.

Examples of conventionally employed bases are sodium hydroxide, potassium hydroxide, sodium and potassium carbonate, sodium methylate and sodium hydride, the reaction preferably being carried out in the presence of potassium carbonate or sodium hydride.

The preparation of N-(3-hydroxyphenyl)tetrahydroindazole derivatives IIa has been disclosed (EP-A 105,721). It takes place in 4 stages starting from the appropriate nitrophenol derivative IVa as shown below.

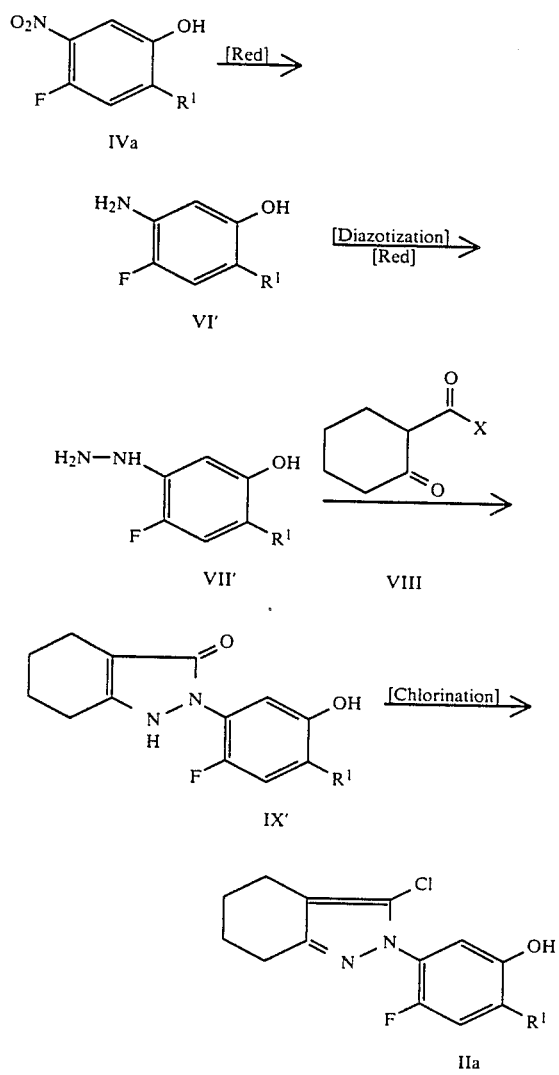

The N-(3-hydroxyphenyl)tetrahydroindazole derivatives IIb are obtained in a similar manner in 6 stages starting from an appropriate nitrophenol derivative IVb, with formation as intermediate of the compounds Ib where $R^3$ is $C_1$-$C_4$-alkyl (Alk), as shown below.

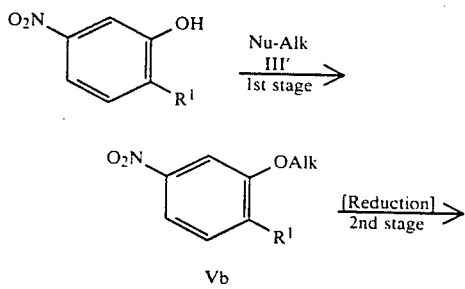

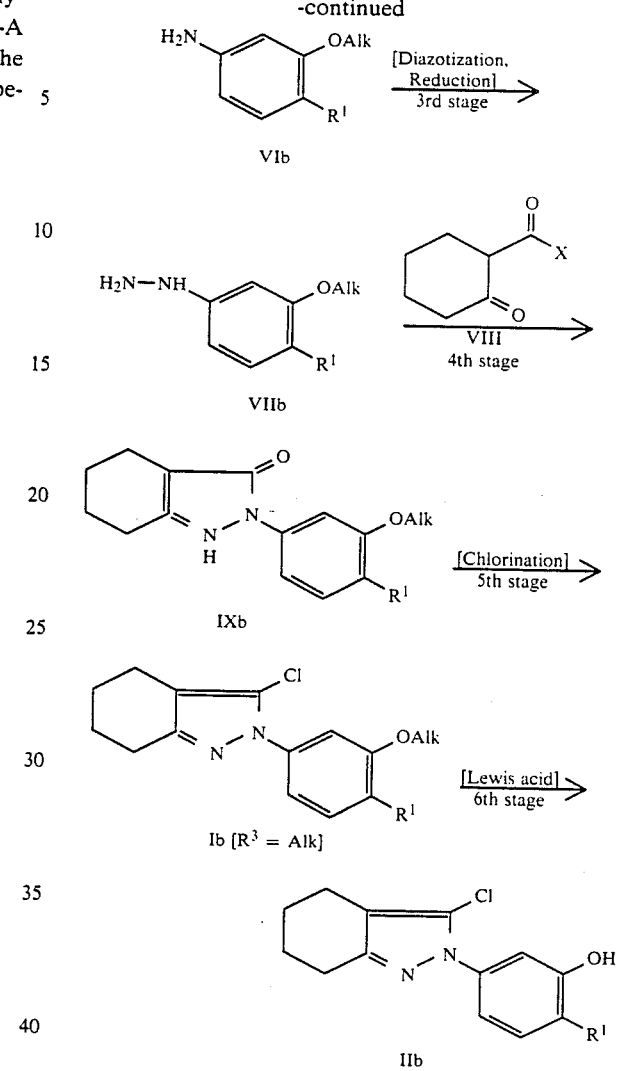

It is advisable, for the preparation of compounds Ib in which $R^3$ is unstable under the chlorination conditions (5th stage), to etherify the alcohol IIb with the compound IIIb under conditions similar to those described for the reaction of IIa with IIIa. Compounds Ib in which $R^3$ is stable to these reaction conditions can be prepared in a manner similar to that shown above.

The individual reaction stages are carried out by conventional methods.

The reaction conditions for the 1st stage (etherification) are, in general and in particular, the same as for the reaction of IIa or IIb with IIIa or IIIb as described above.

This reaction is preferably carried out in acetone, acetonitrile and/or dimethylformamide in the presence of sodium hydride or potassium carbonate as base at from 25° to 150° C.

The reduction of the nitrophenyl ethers Vb to the corresponding aniline derivatives VIb is carried out by conventional methods, for example in the presence of inorganic reducing agents such as Raney nickel, iron or tin(II) salts, in aprotic or protic polar solvents or in the presence of hydrogen on noble metal catalysts such as platinum and palladium in aprotic polar solvents.

The isolated aniline derivative IIb is then diazotized with a nitrite in an inert solvent in a conventional manner at from −50° C. to 50° C. and subsequently reduced in situ.

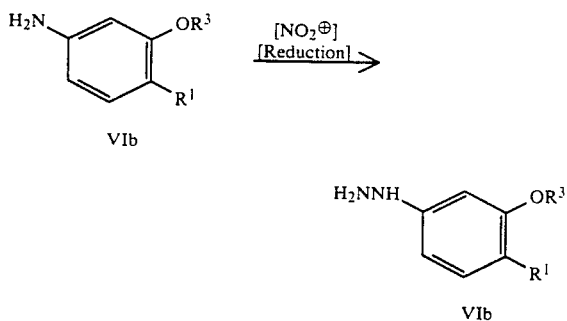

When an inorganic nitrite, such as nitrous acid and alkali metal nitrites, is used for the diazotization, it is preferably carried out in aqueous phase with the addition of mineral acids at from −10° C. to 5° C., whereas diazotization with the conventional organic nitrites, such as amyl nitrite, is preferably carried out in an aprotic polar solution at from −10° C. to 25° C.

Irrespective of the diazotization method, in situ reduction to the corresponding phenylhydrazine VIIb is possible. For this, an inorganic reducing agent such as a tin(II) salt, an alkali metal sulfite, an alkali metal bisulfite and sulfur dioxide is added, as the substance or in solution, to the resulting reaction mixture at from −20° C. to 25° C.

The phenylhydrazine derivative VIIb obtained in this way is subsequently cyclized with a cyclohexanone derivative VIII in an inert organic solvent at up to 200° C., preferably at from 25° C. to 150° C., in the presence or absence of a base.

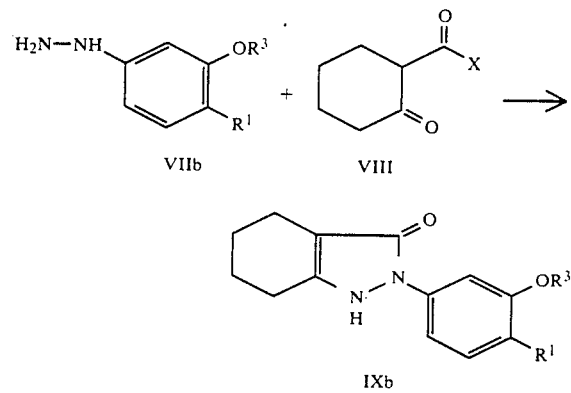

X in formula VIII is a nucleophilic leaving group. Suitable examples of this are halogen such as chlorine and bromine, alkoxy such as methoxy, ethoxy, propyloxy and isopropyloxy, and sulfonates such as tosylate.

Depending on the meaning of X, the reaction is carried out in protic or aprotic polar or aprotic nonpolar solvents in the presence or absence of a base.

Where X is halogen, it is preferably carried out in the presence of a base in an aprotic polar or aprotic nonpolar solvent.

Particularly suitable bases for this are tertiary amines such as triethylamine, diisopropylethylamine, N,N-dimethylaniline, N,N-dimethyl-p-aminopyridine, pyridine, isoquinoline, N-methylpyrrolidine, N,N,N',N'-tetramethylethylenediamine, 1,5-diazabicyclo[4.3.0]non-5-ene (DBN) and 1,8-diazabicyclo[5.4.0]undec-7-ene (DBU).

Examples of suitable solvents are toluene, xylene, chloroform and tetrahydrofuran, and corresponding mixtures.

Toluene or chloroform is preferably used in the presence of triethylamine, pyridine or DBU as base.

Where X is an alcoholate or sulfonate, protic polar solvents such as, in particular, glacial acetic acid are preferred. In this case the reaction is carried out without addition of a base.

The indazole derivative IXb obtained in this way is chlorinated to the N-phenyltetrahydroindazole derivative Ib ($R^3$=alkyl) in a conventional manner using a conventional chlorinating reagent.

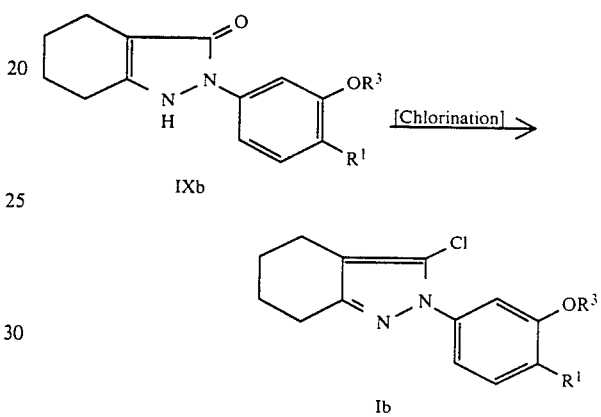

This reaction takes place at up to 200° C., preferably from 50° to 180° C., in the presence of an inert organic solvent and in the presence or absence of a base.

Examples of suitable chlorinating agents are oxychlorides such as phosphorus oxytrichloride, thionyl chloride, phosgene or trichloromethyl chloroformate, as well as chlorides such as phosphorus trichloride, phosphorus pentachloride or sulfur tetrachloride. Phosphorus oxytrichloride is preferably used.

Examples of suitable solvents are toluene, xylene, chloroform and methylene chloride, in particular toluene and chloroform.

Suitable bases are the abovementioned tertiary amines.

The reaction with phosphorus oxytrichloride without added solvent and the reaction with trichloromethyl chloroformate in toluene or chloroform as solvent are particularly preferred.

The derivatives Ib in which $R^3$ is unstable under the conditions described above can be obtained from these N-phenyltetrahydroindazole derivatives Ib according to the invention, in which $R^3$ is $C_1$-$C_4$-alkyl (alk), in conventional ways by ether cleavage and subsequent etherification.

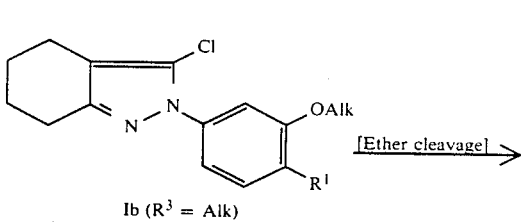

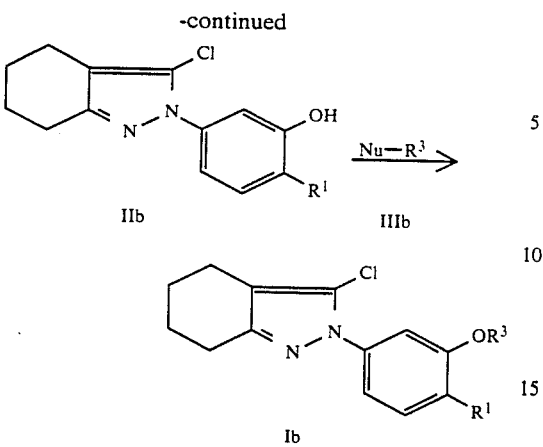

For the ether cleavage the N-alkoxyphenyltetrahydroindazole derivative Ib ($R^3$=alk) is reacted in a conventional manner with a Lewis acid in an inert organic solvent at from 0° C. to 150° C.

Examples of particularly suitable Lewis acids for this are boron trifluoride and its etherate, aluminum trichloride, phosphorus trichloride and boron tribromide.

Preferred solvents are ethers such as tetrahydrofuran, halogenated hydrocarbons such as chloroform and hydrocarbons such as toluene and corresponding mixtures.

The subsequent reaction of the N-(3-hydroxyphenyl)-tetrahydroindazole IIb with the nucleophilic reagent IIIb is carried out under conditions similar to those described above for the reaction of IIa and IIIa.

With regard to the intended use of the compounds Ia and Ib, the following substituents are suitable:

$R^1$ is halogen such as fluorine, chlorine and bromine, in particular chlorine;

$R^2$ is alkoxycarbonylalkenyl such as 2-methoxycarbonyl-2-propenyl, 2-ethoxycarbonyl-2-propenyl, 2-propyloxycarbonyl-2-propenyl, 2-(i-propyloxycarbonyl)-2-propenyl, 2-methoxycarbonyl-2-butenyl, 2-ethoxycarbonyl-2-butenyl, 2-propyloxycarbonyl-2-butenyl, 2-(i-propyloxycarbonyl)-2-butenyl;

alkyl such as methyl, ethyl, propyl and 1-methylethyl, preferably methyl and ethyl, which is substituted in the 1 or 2 position by one of the following:

alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl and 1,1-dimethylethoxycarbonyl;

or a 5- or 6-membered saturated or singly unsaturated heterocycle which contains an oxygen or sulfur, such as tetrahydrofuranyl, tetrahydrothienyl, 2,3-dihydrofuranyl, 2,5-dihydrofuranyl, 2,3-dihydrothienyl, 2,5-dihydrothienyl, tetrahydropyranyl, tetrahydrothiopyranyl, 2H-3,4-dihydropyranyl, 2H-5,6-dihydropyranyl, 2H-3,4-dihydrothiopyranyl and 2H-5,6-dihydrothiopyranyl, preferably tetrahydrofuranyl, tetrahydrothienyl, tetrahydropyranyl, tetrahydrothiopyranyl, 2H-3,4-dihydropyranyl, 2H-5,6-dihydropyranyl, 2H-3,4-dihydrothiopyranyl and 2H-5,6-dihydrothiopyranyl, it being possible for these rings to be substituted by up to 4 of the alkyls mentioned under $R^2$, preferably by one to four methyls; all possible steric arrangements may occur in the case of substituted rings;

$R^3$ is alkyl such as ethyl, propyl, 1-methylethyl, butyl, 1-methylpropyl, 2-methylpropyl and 1,1-dimethylethyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl and 1-ethyl-2-methylpropyl, as well as the isomeric heptyls;

alkenyl such as 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,1-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2methyl-2-propenyl;

alkynyl such as 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

or an $R^2$ which has, in general and in particular, the abovementioned meaning.

Specific examples of particularly active compounds Ia and Ib are listed in Tables A, B and C which follow.

TABLE A

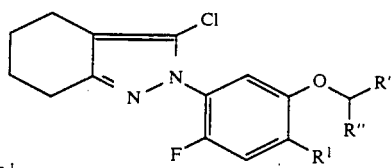

Ia

| R¹ | R' | R" |
|---|---|---|
| Cl | H | CO₂CH₃ |
| Cl | CH₃ | CO₂CH₃ |
| Br | H | CO₂CH₃ |
| Br | CH₃ | CO₂CH₃ |
| Cl | H | CO₂CH₂CH₃ |
| Cl | CH₃ | CO₂CH₂CH₃ |
| Br | H | CO₂CH₂CH₃ |
| Br | CH₃ | CO₂CH₂CH₃ |
| Cl | H | CO₂CH(CH₃)₂ |
| Cl | CH₃ | CO₂CH(CH₃)₂ |
| Br | H | CO₂CH(CH₃)₂ |
| Br | CH₃ | CO₂CH(CH₃)₂ |
| Cl | H | CH=CH—CO₂CH₃ |
| Cl | CH₃ | CH=CH—CO₂CH₃ |
| Br | H | CH=CH—CO₂CH₃ |
| Br | CH₃ | CH=CH—CO₂CH₃ |
| Cl | H | CH=CH—CO₂CH₂CH₃ |
| Cl | CH₃ | CH=CH—CO₂CH₂CH₃ |
| Br | H | CH=CH—CO₂CH₂CH₃ |
| Br | CH₃ | CH=CH—CO₂CH₂CH₃ |
| Cl | H | CH=CH—CO₂CH(CH₃)₂ |
| Cl | CH₃ | CH=CH—CO₂CH(CH₃)₂ |
| Br | H | CH=CH—CO₂CH(CH₃)₂ |
| Br | CH₃ | CH=CH—CO₂CH(CH₃)₂ |
| Cl | H | CH₂CO₂CH₃ |
| Cl | CH₃ | CH₂CO₂CH₃ |
| Br | H | CH₂CO₂CH₃ |
| Br | CH₃ | CH₂CO₂CH₃ |
| Cl | H | CH₂CO₂CH₂CH₃ |
| Cl | CH₃ | CH₂CO₂CH₂CH₃ |
| Br | H | CH₂CO₂CH₂CH₃ |
| Br | CH₃ | CH₂CO₂CH₂CH₃ |
| Cl | H | CH₂CO₂CH(CH₃)₂ |
| Cl | CH₃ | CH₂CO₂CH(CH₃)₂ |
| Br | H | CH₂CO₂CH(CH₃)₂ |
| Br | CH₃ | CH₂CO₂CH(CH₃)₂ |
| Cl | H | CH=C(CH₃)—CO₂CH₃ |
| Cl | CH₃ | CH=C(CH₃)—CO₂CH₃ |
| Br | H | CH=C(CH₃)—CO₂CH₃ |
| Br | CH₃ | CH=C(CH₃)—CO₂CH₃ |
| Cl | H | CH=C(CH₃)—CO₂CH₂CH₃ |
| Cl | CH₃ | CH=C(CH₃)—CO₂CH₂CH₃ |
| Br | H | CH=C(CH₃)—CO₂CH₂CH₃ |
| Br | CH₃ | CH=C(CH₃)—CO₂CH₂CH₃ |
| Cl | H | CH=C(CH₃)—CO₂CH(CH₃)₂ |
| Cl | CH₃ | CH=C(CH₃)—CO₂CH(CH₃)₂ |
| Br | H | CH=C(CH₃)—CO₂CH(CH₃)₂ |
| Br | CH₃ | CH=C(CH₃)—CO₂CH(CH₃)₂ |
| Cl | H | (2-tetrahydrofuranyl) |
| Cl | CH₃ | (2-tetrahydrofuranyl) |
| Br | H | (2-tetrahydrofuranyl) |
| Br | CH₃ | (2-tetrahydrofuranyl) |
| Cl | H | (3-tetrahydrofuranyl) |

TABLE A-continued

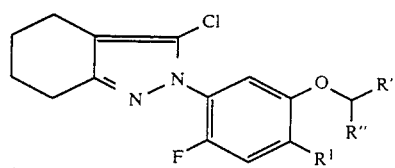

Ia

| R¹ | R' | R" |
|---|---|---|
| Cl | CH₃ | (3-tetrahydrofuranyl) |
| Br | H | (3-tetrahydrofuranyl) |
| Br | CH₃ | (3-tetrahydrofuranyl) |
| Cl | H | (2,5-dihydrofuranyl) |
| Cl | CH₃ | (2,5-dihydrofuranyl) |
| Br | H | (2,5-dihydrofuranyl) |
| Br | CH₃ | (2,5-dihydrofuranyl) |
| Cl | H | (2-tetrahydrothienyl) |
| Cl | CH₃ | (2-tetrahydrothienyl) |
| Br | H | (2-tetrahydrothienyl) |
| Br | CH₃ | (2-tetrahydrothienyl) |
| Cl | H | (2-tetrahydropyranyl) |
| Cl | CH₃ | (2-tetrahydropyranyl) |

TABLE A-continued

Ia

[Structure: 3-chloro-4,5,6,7-tetrahydro-2H-indazole substituted with a phenyl group bearing F, R¹, and O-CHR'R'' substituents]

| R¹ | R' | R'' |
|---|---|---|
| Br | H | tetrahydropyran-2-yl |
| Br | CH₃ | tetrahydropyran-2-yl |
| Cl | H | tetrahydropyran-3-yl |
| Cl | CH₃ | tetrahydropyran-3-yl |
| Br | H | tetrahydropyran-3-yl |
| Br | CH₃ | tetrahydropyran-3-yl |
| Cl | H | tetrahydropyran-4-yl |
| Cl | CH₃ | tetrahydropyran-4-yl |
| Br | H | tetrahydropyran-4-yl |
| Br | CH₃ | tetrahydropyran-4-yl |
| Cl | H | 2-methyl-tetrahydropyran-2-yl |
| Cl | CH₃ | 2-methyl-tetrahydropyran-2-yl |
| Br | H | 2-methyl-tetrahydropyran-2-yl |
| Br | CH₃ | 2-methyl-tetrahydropyran-2-yl |
| Cl | H | 3-methyl-tetrahydropyran-4-yl |
| Cl | CH₃ | 3-methyl-tetrahydropyran-4-yl |
| Br | H | 3-methyl-tetrahydropyran-4-yl |
| Br | CH₃ | 3-methyl-tetrahydropyran-4-yl |
| Cl | H | tetrahydrothiopyran-2-yl |
| Cl | CH₃ | tetrahydrothiopyran-2-yl |
| Br | H | tetrahydrothiopyran-2-yl |
| Br | CH₃ | tetrahydrothiopyran-2-yl |

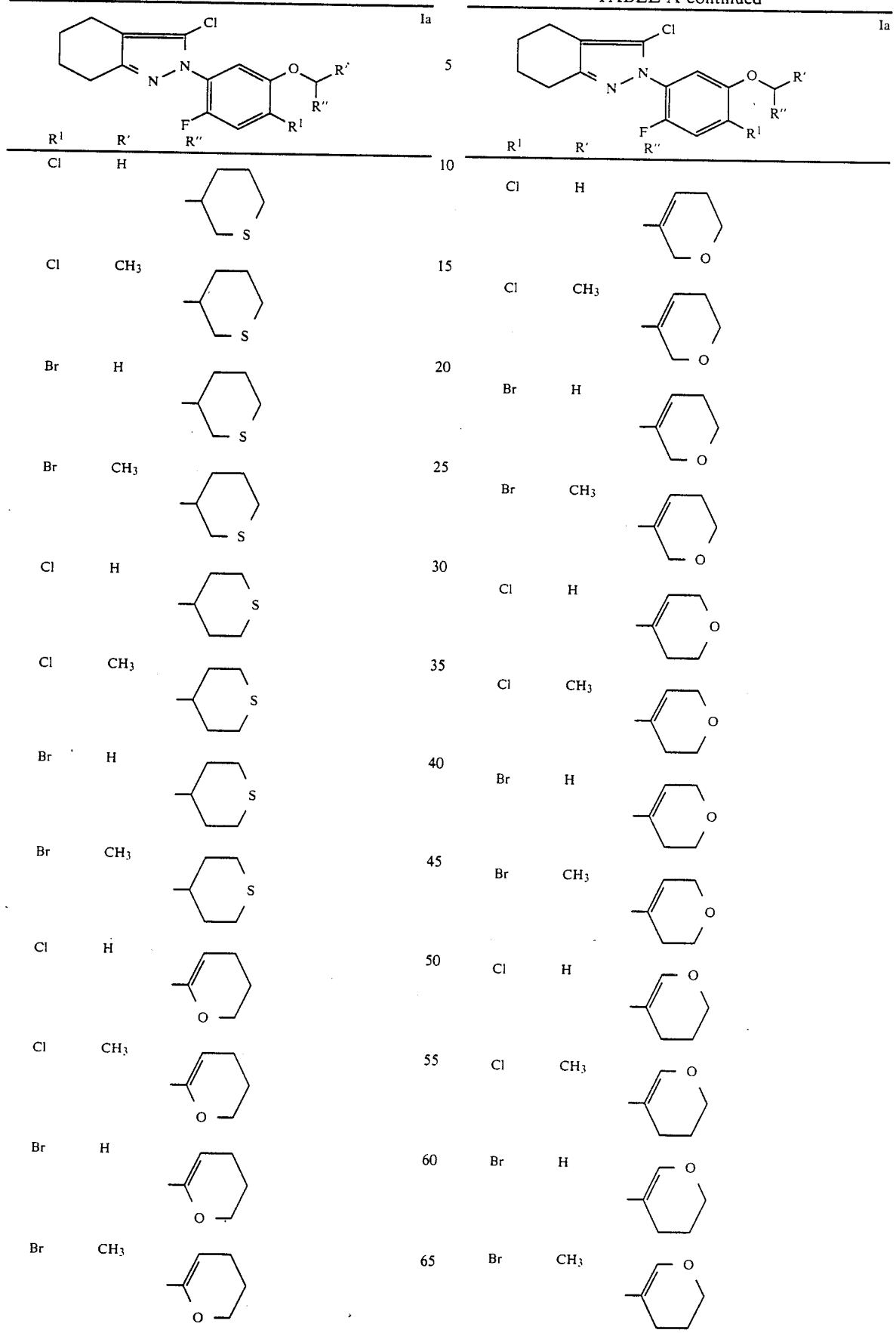

TABLE A-continued
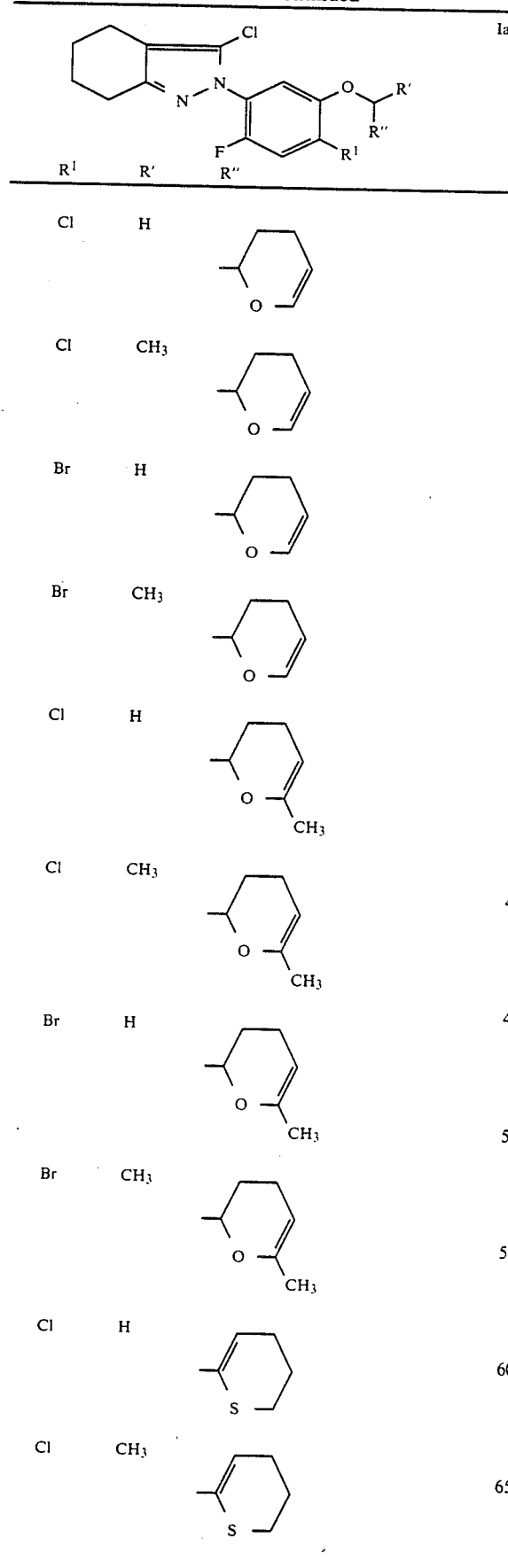
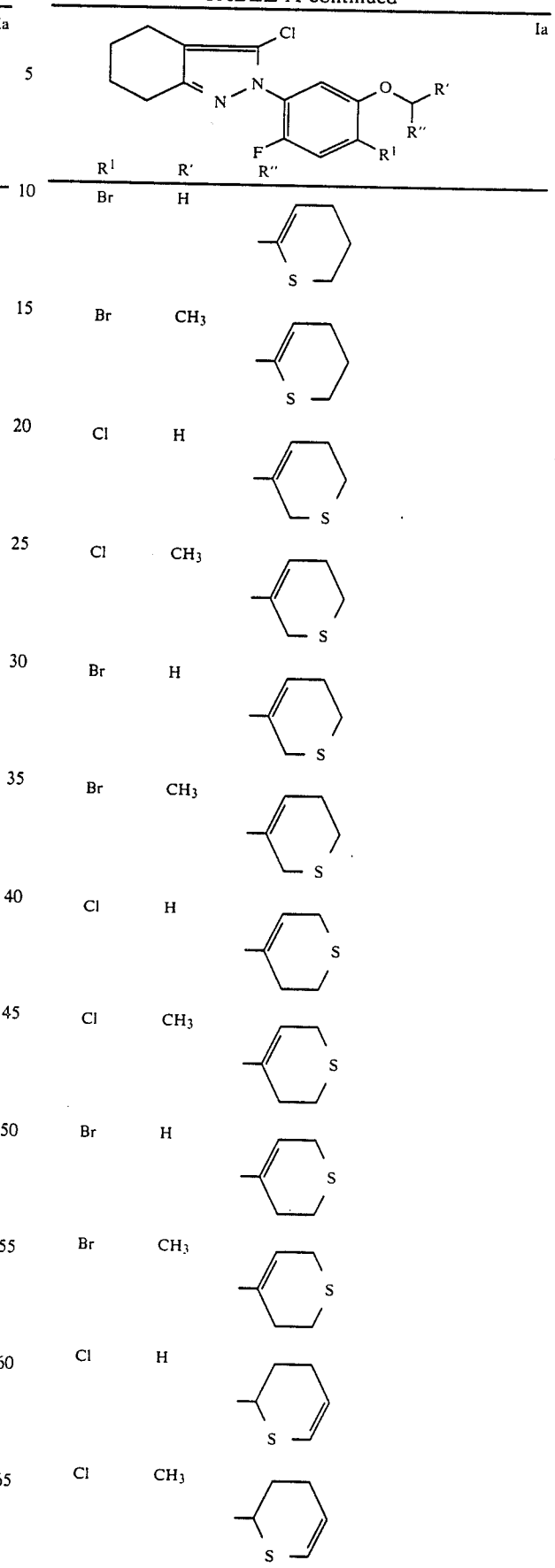

TABLE A-continued

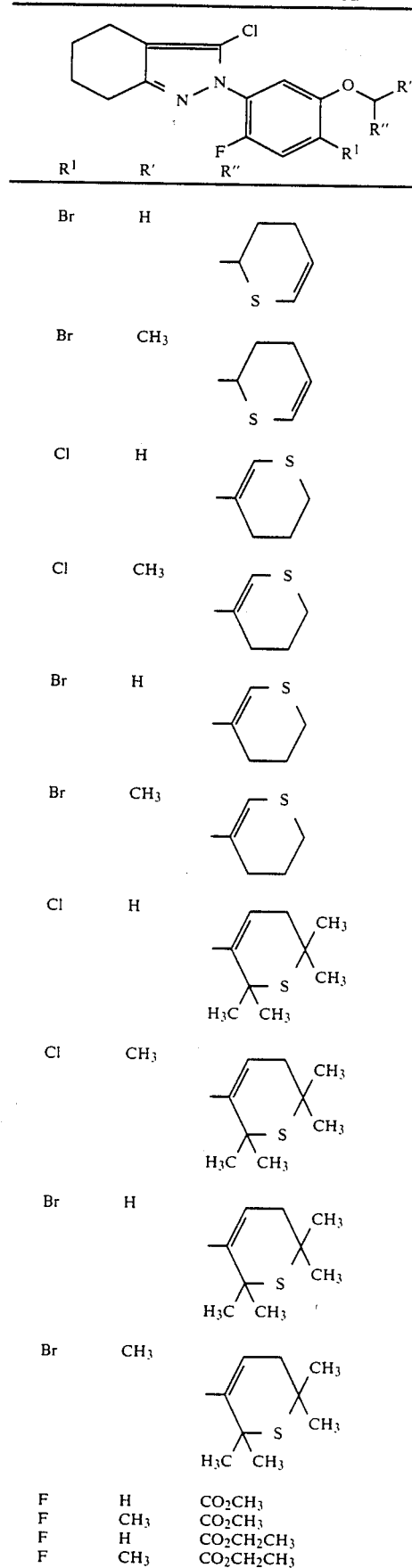

| R¹ | R' | R'' |
|---|---|---|
| Br | H | |
| Br | CH₃ | |
| Cl | H | |
| Cl | CH₃ | |
| Br | H | |
| Br | CH₃ | |
| Cl | H | |
| Cl | CH₃ | |
| Br | H | |
| Br | CH₃ | |
| F | H | CO₂CH₃ |
| F | CH₃ | CO₂CH₃ |
| F | H | CO₂CH₂CH₃ |
| F | CH₃ | CO₂CH₂CH₃ |

TABLE A-continued

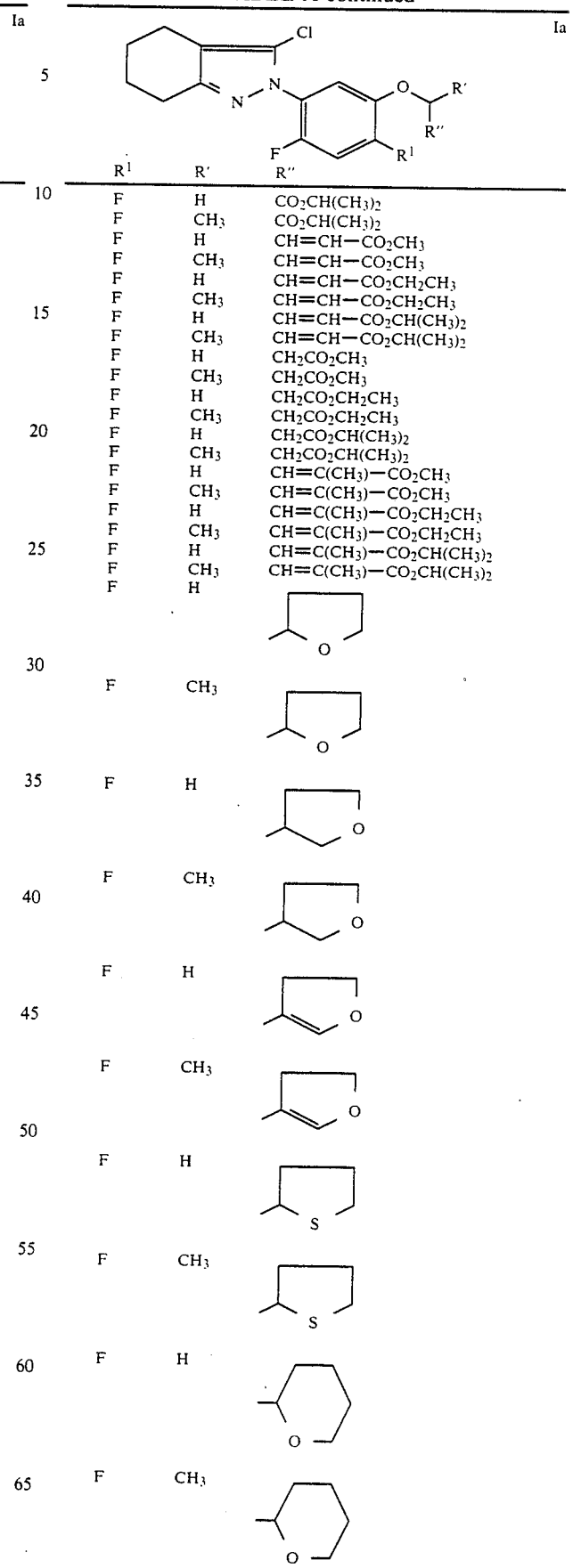

| R¹ | R' | R'' |
|---|---|---|
| F | H | CO₂CH(CH₃)₂ |
| F | CH₃ | CO₂CH(CH₃)₂ |
| F | H | CH=CH—CO₂CH₃ |
| F | CH₃ | CH=CH—CO₂CH₃ |
| F | H | CH=CH—CO₂CH₂CH₃ |
| F | CH₃ | CH=CH—CO₂CH₂CH₃ |
| F | H | CH=CH—CO₂CH(CH₃)₂ |
| F | CH₃ | CH=CH—CO₂CH(CH₃)₂ |
| F | H | CH₂CO₂CH₃ |
| F | CH₃ | CH₂CO₂CH₃ |
| F | H | CH₂CO₂CH₂CH₃ |
| F | CH₃ | CH₂CO₂CH₂CH₃ |
| F | H | CH₂CO₂CH(CH₃)₂ |
| F | CH₃ | CH₂CO₂CH(CH₃)₂ |
| F | H | CH=C(CH₃)—CO₂CH₃ |
| F | CH₃ | CH=C(CH₃)—CO₂CH₃ |
| F | H | CH=C(CH₃)—CO₂CH₂CH₃ |
| F | CH₃ | CH=C(CH₃)—CO₂CH₂CH₃ |
| F | H | CH=C(CH₃)—CO₂CH(CH₃)₂ |
| F | CH₃ | CH=C(CH₃)—CO₂CH(CH₃)₂ |
| F | H | |
| F | CH₃ | |
| F | H | |
| F | CH₃ | |
| F | H | |
| F | CH₃ | |
| F | H | |
| F | CH₃ | |
| F | H | |
| F | CH₃ | |

TABLE A-continued

Structure Ia: 3-chloro-4,5,6,7-tetrahydro-2H-indazole N-substituted with phenyl bearing F, OCHR'R'', and R¹.

| R¹ | R' | R'' |
|---|---|---|
| F | H | 3-tetrahydropyranyl (O at 1-position) |
| F | CH₃ | 3-tetrahydropyranyl |
| F | H | 4-tetrahydropyranyl |
| F | CH₃ | 4-tetrahydropyranyl |
| F | H | 6,6-dimethyl-tetrahydropyran-2-yl |
| F | CH₃ | 6,6-dimethyl-tetrahydropyran-2-yl |
| F | H | 3-methyl-4-tetrahydropyranyl |
| F | CH₃ | 3-methyl-4-tetrahydropyranyl |
| F | H | 2-tetrahydrothiopyranyl |
| F | CH₃ | 2-tetrahydrothiopyranyl |
| F | H | 3-tetrahydrothiopyranyl |
| F | CH₃ | 3-tetrahydrothiopyranyl |
| F | H | 4-tetrahydrothiopyranyl |
| F | CH₃ | 4-tetrahydrothiopyranyl |
| F | H | 2-(3,4-dihydro-2H-pyranyl) |
| F | CH₃ | 2-(3,4-dihydro-2H-pyranyl) |
| F | H | 3-(3,6-dihydro-2H-pyranyl) |
| F | CH₃ | 3-(3,6-dihydro-2H-pyranyl) |
| F | H | 4-(3,6-dihydro-2H-pyranyl) |
| F | CH₃ | 4-(3,6-dihydro-2H-pyranyl) |
| F | H | 4-(3,4-dihydro-2H-pyranyl) |
| F | CH₃ | 4-(3,4-dihydro-2H-pyranyl) |
| F | H | 2-(5,6-dihydro-2H-pyranyl) |

TABLE A-continued

Structure Ia: 3-chloro-4,5,6,7-tetrahydro-2H-indazole with N2 attached to a phenyl group bearing F (ortho to N), R¹, and OCH(R')(R'') substituents.

| R¹ | R' | R'' |
|---|---|---|
| F | CH₃ | 3,4-dihydro-2H-pyran-6-yl |
| F | H | 3,4-dihydro-2H-pyran-2-yl |
| F | CH₃ | 3,4-dihydro-2H-pyran-2-yl |
| F | H | 6-methyl-3,4-dihydro-2H-pyran-2-yl |
| F | CH₃ | 6-methyl-3,4-dihydro-2H-pyran-2-yl |
| F | H | 3,4-dihydro-2H-thiopyran-6-yl |
| F | CH₃ | 3,4-dihydro-2H-thiopyran-6-yl |
| F | H | 5,6-dihydro-2H-thiopyran-3-yl |
| F | CH₃ | 5,6-dihydro-2H-thiopyran-3-yl |
| F | H | 5,6-dihydro-2H-thiopyran-4-yl |
| F | CH₃ | 5,6-dihydro-2H-thiopyran-4-yl |
| F | H | 3,4-dihydro-2H-thiopyran-2-yl |
| F | CH₃ | 3,4-dihydro-2H-thiopyran-2-yl |
| F | H | 3,6-dihydro-2H-thiopyran-2-yl |
| F | CH₃ | 3,6-dihydro-2H-thiopyran-2-yl |
| F | H | 3,3,6,6-tetramethyl-3,6-dihydro-2H-thiopyran-4-yl |
| F | CH₃ | 3,3,6,6-tetramethyl-3,6-dihydro-2H-thiopyran-4-yl |

TABLE 8

Structure Ib: 3-chloro-4,5,6,7-tetrahydro-2H-indazole with N2 attached to a phenyl group bearing OR³ and R¹ substituents.

| R¹ | R³ |
|---|---|
| Br | CH₃ |
| Cl | CH₂CH₃ |
| Br | CH₂CH₃ |
| Cl | (CH₂)₂CH₃ |
| Br | (CH₂)₂CH₃ |
| Cl | CH(CH₃)₂ |
| Br | CH(CH₃)₂ |
| Cl | (CH₂)₃CH₃ |
| Br | (CH₂)₃CH₃ |
| Cl | CH(CH₃)CH₂CH₃ |
| Br | CH(CH₃)CH₂CH₃ |
| Cl | CH₂CH(CH₃)₂ |
| Br | CH₂CH(CH₃)₂ |
| Cl | CH₂CH=CH₂ |
| Br | CH₂CH=CH₂ |
| Cl | CH₂CH=CHCH₃ |
| Br | CH₂CH=CHCH₃ |
| Cl | CH₂C≡CH |
| Br | CH₂C≡CH |

TABLE 8-continued

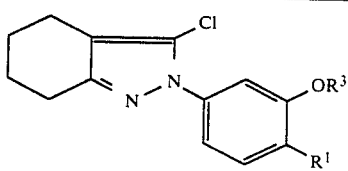

| R¹ | R³ |
|---|---|
| Cl | CH$_2$C≡CCH$_3$ |
| Br | CH$_2$C≡CCH$_3$ |
| F | CH$_3$ |
| F | CH$_2$CH$_3$ |
| F | (CH$_2$)$_2$CH$_3$ |
| F | CH(CH$_3$)$_2$ |
| F | (CH$_2$)$_3$CH$_3$ |
| F | CH(CH$_3$)CH$_2$CH$_3$ |
| F | CH$_2$CH(CH$_3$)$_2$ |
| F | CH$_2$CH=CH$_2$ |
| F | CH$_2$CH=CHCH$_3$ |
| F | CH$_2$C≡CH |
| F | CH$_2$C≡CCH$_3$ |

TABLE C

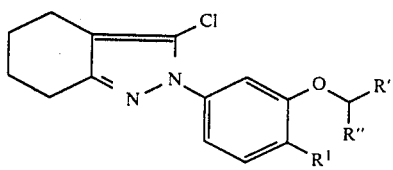

| R¹ | R' | R'' |
|---|---|---|
| Cl | H | CO$_2$CH$_3$ |
| Cl | CH$_3$ | CO$_2$CH$_3$ |
| Br | H | CO$_2$CH$_3$ |
| Br | CH$_3$ | CO$_2$CH$_3$ |
| Cl | H | CO$_2$CH$_2$CH$_3$ |
| Cl | CH$_3$ | CO$_2$CH$_2$CH$_3$ |
| Br | H | CO$_2$CH$_2$CH$_3$ |
| Br | CH$_3$ | CO$_2$CH$_2$CH$_3$ |
| Cl | H | CO$_2$CH(CH$_3$)$_2$ |
| Cl | CH$_3$ | CO$_2$CH(CH$_3$)$_2$ |
| Br | H | CO$_2$CH(CH$_3$)$_2$ |
| Br | CH$_3$ | CO$_2$CH(CH$_3$)$_2$ |
| Cl | H | CH=CH—CO$_2$CH$_3$ |
| Cl | CH$_3$ | CH=CH—CO$_2$CH$_3$ |
| Br | H | CH=CH—CO$_2$CH$_3$ |
| Br | CH$_3$ | CH=CH—CO$_2$CH$_3$ |
| Cl | H | CH=CH—CO$_2$CH$_2$CH$_3$ |
| Cl | CH$_3$ | CH=CH—CO$_2$CH$_2$CH$_3$ |
| Br | H | CH=CH—CO$_2$CH$_2$CH$_3$ |
| Br | CH$_3$ | CH=CH—CO$_2$CH$_2$CH$_3$ |
| Cl | H | CH=CH—CO$_2$CH(CH$_3$)$_2$ |
| Cl | CH$_3$ | CH=CH—CO$_2$CH(CH$_3$)$_2$ |
| Br | H | CH=CH—CO$_2$CH(CH$_3$)$_2$ |
| Br | CH$_3$ | CH=CH—CO$_2$CH(CH$_3$)$_2$ |
| Cl | H | CH$_2$CO$_2$CH$_3$ |
| Cl | CH$_3$ | CH$_2$CO$_2$CH$_3$ |
| Br | H | CH$_2$CO$_2$CH$_3$ |
| Br | CH$_3$ | CH$_2$CO$_2$CH$_3$ |
| Cl | H | CH$_2$CO$_2$CH$_2$CH$_3$ |
| Cl | CH$_3$ | CH$_2$CO$_2$CH$_2$CH$_3$ |
| Br | H | CH$_2$CO$_2$CH$_2$CH$_3$ |
| Br | CH$_3$ | CH$_2$CO$_2$CH$_2$CH$_3$ |
| Cl | H | CH$_2$CO$_2$CH(CH$_3$)$_2$ |
| Cl | CH$_3$ | CH$_2$CO$_2$CH(CH$_3$)$_2$ |
| Br | H | CH$_2$CO$_2$CH(CH$_3$)$_2$ |
| Br | CH$_3$ | CH$_2$CO$_2$CH(CH$_3$)$_2$ |
| Cl | H | CH=C(CH$_3$)CO$_2$CH$_3$ |
| Cl | CH$_3$ | CH=C(CH$_3$)CO$_2$CH$_3$ |
| Br | H | CH=C(CH$_3$)CO$_2$CH$_3$ |
| Br | CH$_3$ | CH=C(CH$_3$)CO$_2$CH$_3$ |
| Cl | H | CH=C(CH$_3$)CO$_2$CH$_2$CH$_3$ |
| Cl | CH$_3$ | CH=C(CH$_3$)CO$_2$CH$_2$CH$_3$ |
| Br | H | CH=C(CH$_3$)CO$_2$CH$_2$CH$_3$ |
| Br | CH$_3$ | CH=C(CH$_3$)CO$_2$CH$_2$CH$_3$ |

TABLE C-continued

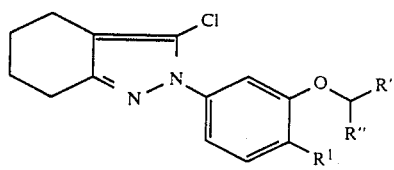

| R¹ | R' | R'' |
|---|---|---|
| Cl | H | CH=C(CH$_3$)CO$_2$CH(CH$_3$)$_2$ |
| Cl | CH$_3$ | CH=C(CH$_3$)CO$_2$CH(CH$_3$)$_2$ |
| Br | H | CH=C(CH$_3$)CO$_2$CH(CH$_3$)$_2$ |
| Br | CH$_3$ | CH=C(CH$_3$)CO$_2$CH(CH$_3$)$_2$ |
| Cl | H | 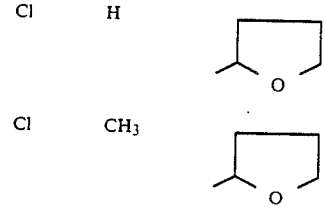 |
| Cl | CH$_3$ | |
| Br | H | |
| Br | CH$_3$ | 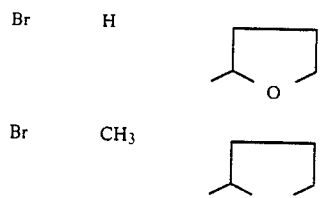 |
| Cl | H | 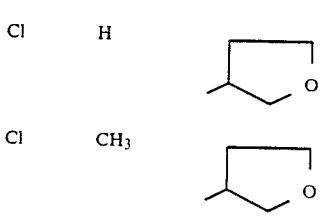 |
| Cl | CH$_3$ | |
| Br | H | |
| Br | CH$_3$ | 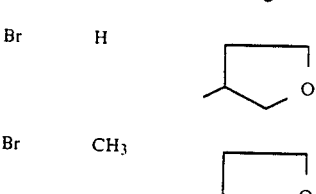 |
| Cl | H | 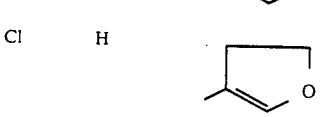 |
| Cl | CH$_3$ | 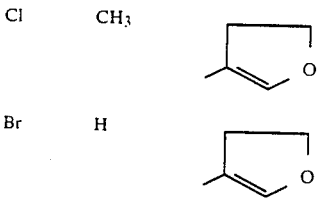 |
| Br | H | |
| Br | CH$_3$ | 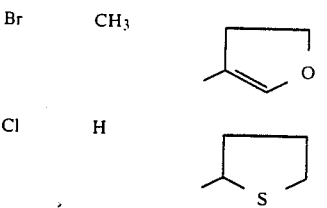 |
| Cl | H | |

TABLE C-continued
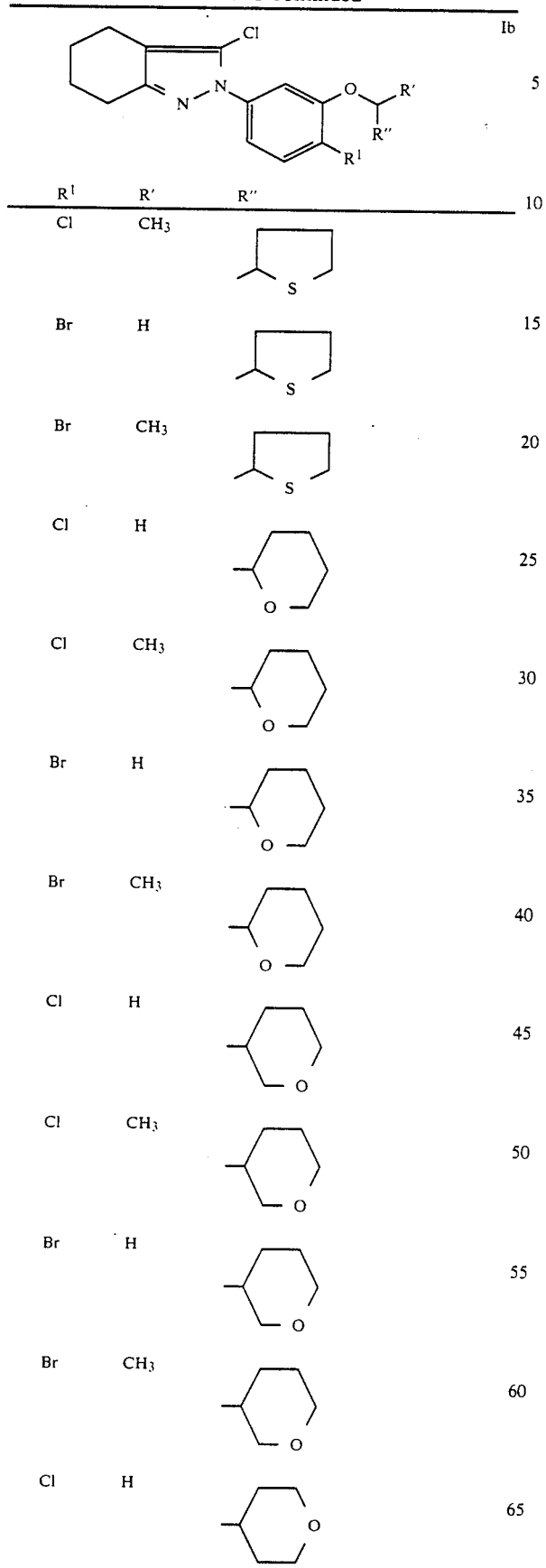
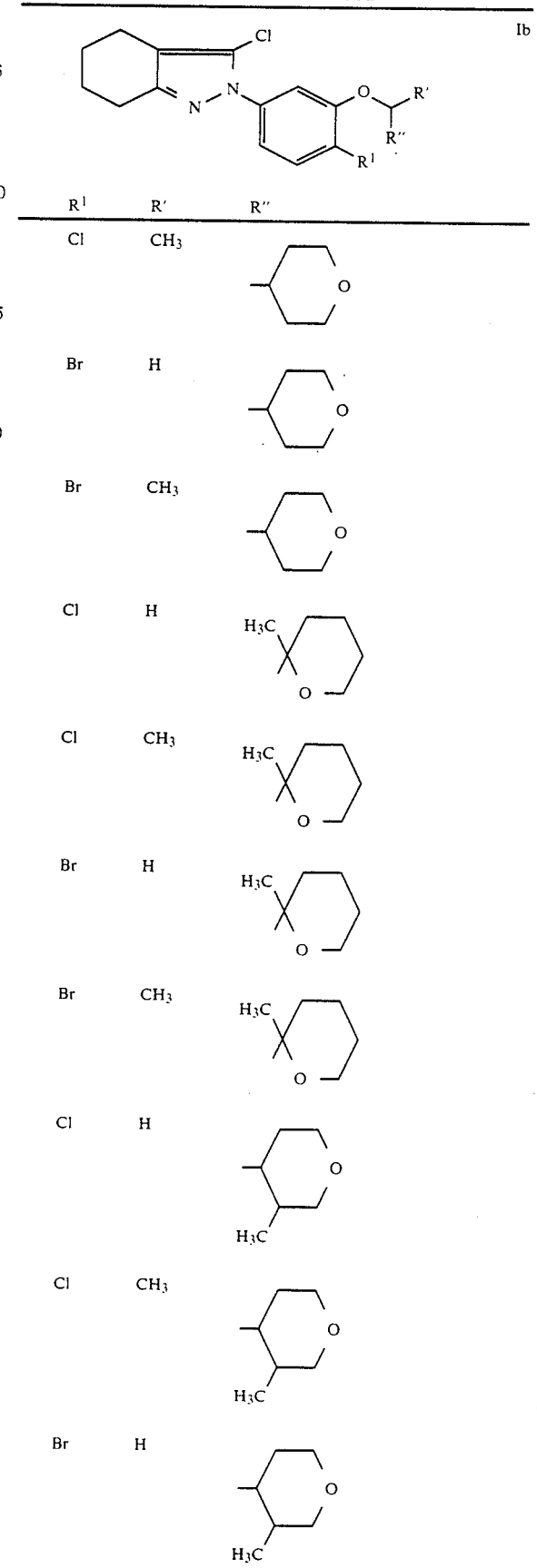

TABLE C-continued
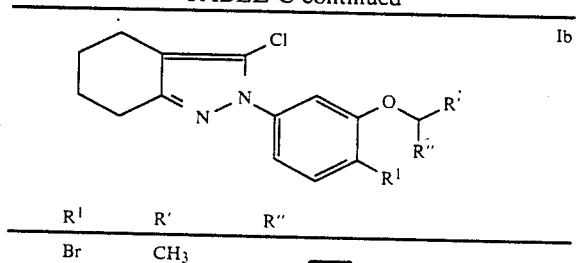
| $R^1$ | $R'$ | $R''$ |
|---|---|---|
| Br | CH₃ | 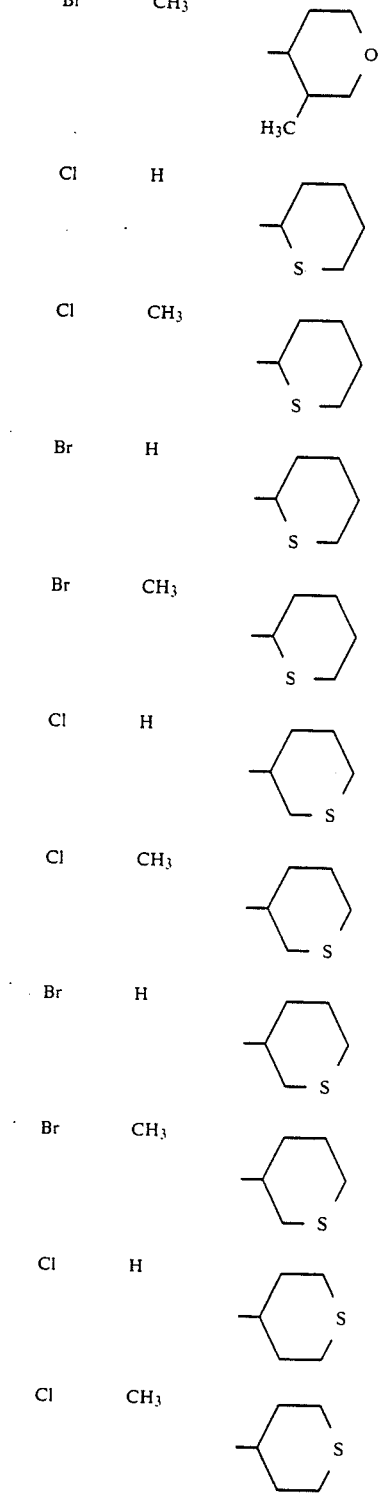 |
| Cl | H | |
| Cl | CH₃ | |
| Br | H | |
| Br | CH₃ | |
| Cl | H | |
| Cl | CH₃ | |
| Br | H | |
| Br | CH₃ | |
| Cl | H | |
| Cl | CH₃ | |
TABLE C-continued
| $R^1$ | $R'$ | $R''$ |
|---|---|---|
| Br | H | 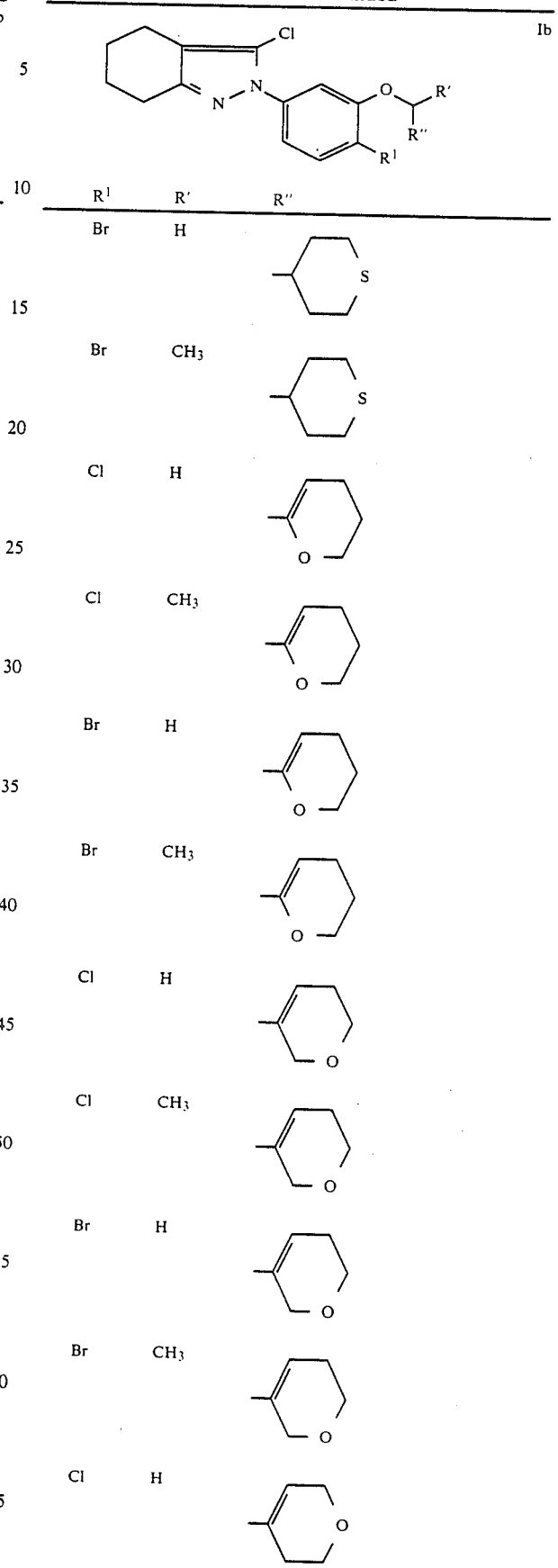 |
| Br | CH₃ | |
| Cl | H | |
| Cl | CH₃ | |
| Br | H | |
| Br | CH₃ | |
| Cl | H | |
| Cl | CH₃ | |
| Br | H | |
| Br | CH₃ | |
| Cl | H | |

TABLE C-continued

Structure Ib: 4,5,6,7-tetrahydro-2H-indazole with 3-Cl, N2 attached to phenyl ring bearing O-CHR'R'' and R¹ substituents.

| R¹ | R' | R'' |
|---|---|---|
| Cl | CH₃ | 4-yl-3,6-dihydro-2H-pyran |
| Br | H | 4-yl-3,6-dihydro-2H-pyran |
| Br | CH₃ | 4-yl-3,6-dihydro-2H-pyran |
| Cl | H | 3-yl-5,6-dihydro-2H-pyran |
| Cl | CH₃ | 3-yl-5,6-dihydro-2H-pyran |
| Br | H | 3-yl-5,6-dihydro-2H-pyran |
| Br | CH₃ | 3-yl-5,6-dihydro-2H-pyran |
| Cl | H | 6-methyl-3,6-dihydro-2H-pyran-5-yl |
| Cl | CH₃ | 6-methyl-3,6-dihydro-2H-pyran-5-yl |
| Br | H | 6-methyl-3,6-dihydro-2H-pyran-5-yl |
| Br | CH₃ | 6-methyl-3,6-dihydro-2H-pyran-5-yl |
| Cl | H | 3,4-dihydro-2H-thiopyran-6-yl |
| Cl | CH₃ | 3,4-dihydro-2H-thiopyran-6-yl |
| Br | H | 3,4-dihydro-2H-thiopyran-6-yl |
| Br | CH₃ | 3,4-dihydro-2H-thiopyran-6-yl |
| Cl | H | 3,6-dihydro-2H-thiopyran-5-yl |
| Cl | CH₃ | 3,6-dihydro-2H-thiopyran-5-yl |
| Br | H | 3,6-dihydro-2H-thiopyran-5-yl |
| Br | CH₃ | 3,6-dihydro-2H-thiopyran-5-yl |
| Cl | H | 3,6-dihydro-2H-thiopyran-4-yl |
| Cl | CH₃ | 3,6-dihydro-2H-thiopyran-4-yl |

TABLE C-continued

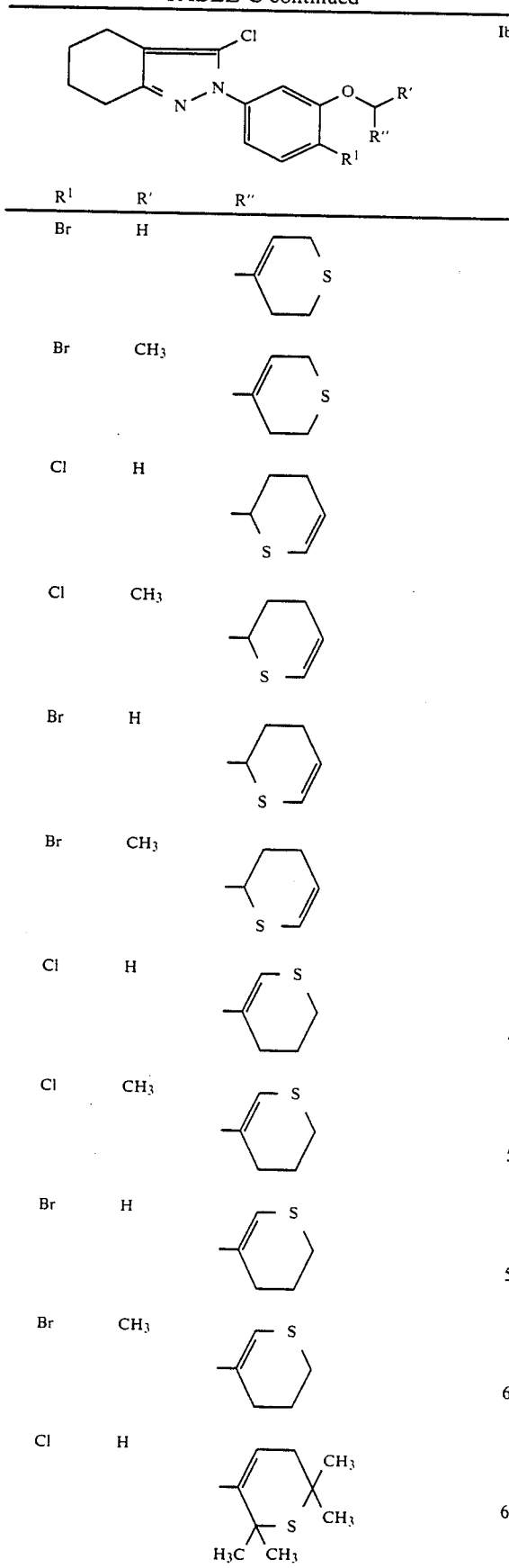

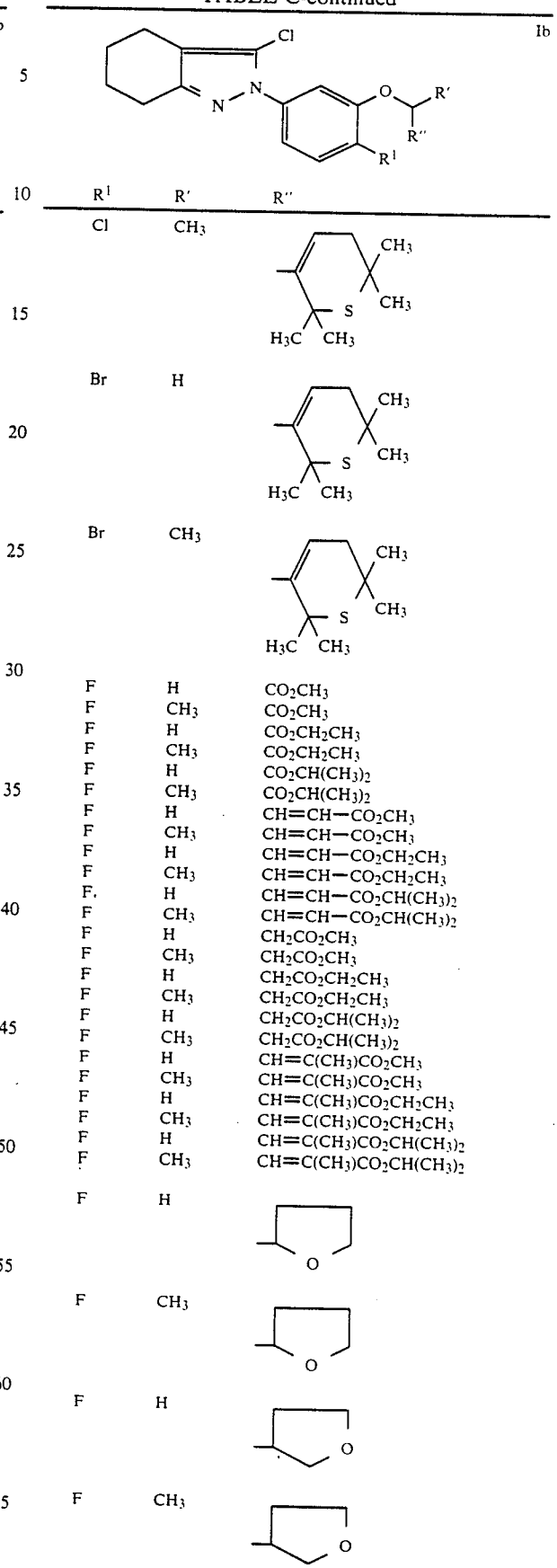

| R¹ | R' | R'' |
|---|---|---|
| F | H | $CO_2CH_3$ |
| F | CH₃ | $CO_2CH_3$ |
| F | H | $CO_2CH_2CH_3$ |
| F | CH₃ | $CO_2CH_2CH_3$ |
| F | H | $CO_2CH(CH_3)_2$ |
| F | CH₃ | $CO_2CH(CH_3)_2$ |
| F | H | $CH=CH-CO_2CH_3$ |
| F | CH₃ | $CH=CH-CO_2CH_3$ |
| F | H | $CH=CH-CO_2CH_2CH_3$ |
| F | CH₃ | $CH=CH-CO_2CH_2CH_3$ |
| F | H | $CH=CH-CO_2CH(CH_3)_2$ |
| F | CH₃ | $CH=CH-CO_2CH(CH_3)_2$ |
| F | H | $CH_2CO_2CH_3$ |
| F | CH₃ | $CH_2CO_2CH_3$ |
| F | H | $CH_2CO_2CH_2CH_3$ |
| F | CH₃ | $CH_2CO_2CH_2CH_3$ |
| F | H | $CH_2CO_2CH(CH_3)_2$ |
| F | CH₃ | $CH_2CO_2CH(CH_3)_2$ |
| F | H | $CH=C(CH_3)CO_2CH_3$ |
| F | CH₃ | $CH=C(CH_3)CO_2CH_3$ |
| F | H | $CH=C(CH_3)CO_2CH_2CH_3$ |
| F | CH₃ | $CH=C(CH_3)CO_2CH_2CH_3$ |
| F | H | $CH=C(CH_3)CO_2CH(CH_3)_2$ |
| F | CH₃ | $CH=C(CH_3)CO_2CH(CH_3)_2$ |

TABLE C-continued
| R¹ | R' | R'' |
|---|---|---|
| F | H | 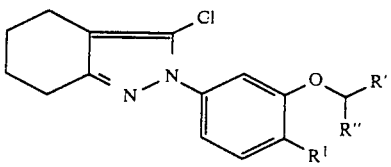 |
| F | CH₃ | 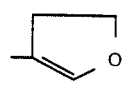 |
| F | H | 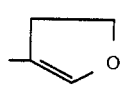 |
| F | CH₃ | 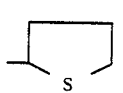 |
| F | H |  |
| F | CH₃ |  |
| F | H |  |
| F | CH₃ | 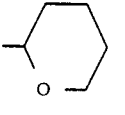 |
| F | H |  |
| F | CH₃ | 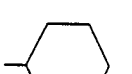 |
| F | H | 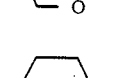 |
| F | CH₃ | 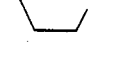 |
| F | H | 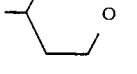 |
| F | CH₃ | 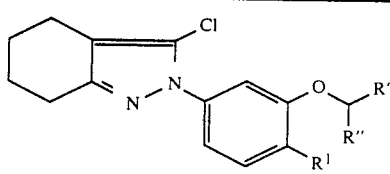 |
| F | H |  |
| F | CH₃ | 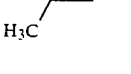 |
| F | H | 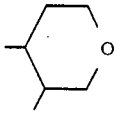 |
| F | CH₃ |  |
| F | H | 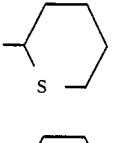 |
| F | CH₃ | 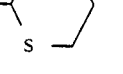 |
| F | H | 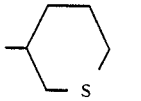 |
| F | CH₃ | 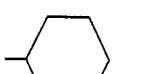 |
| F | H | 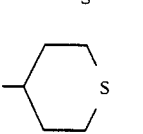 |
| F | CH₃ |  |
| F | H | 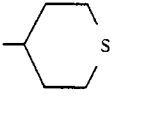 |

TABLE C-continued

Structure Ib: 3-chloro-tetrahydroindazole with N-phenyl bearing OCHR'R" and R¹ substituents.

| R¹ | R' | R" |
|---|---|---|
| F | CH₃ | 3,6-dihydro-2H-pyran-4-yl (O in ring) |
| F | H | 3,6-dihydro-2H-pyran-4-yl |
| F | CH₃ | 3,4-dihydro-2H-pyran-5-yl |
| F | H | 3,4-dihydro-2H-pyran-5-yl |
| F | CH₃ | 3,4-dihydro-2H-pyran-6-yl |
| F | H | 6-methyl-3,4-dihydro-2H-pyran-2-yl |
| F | CH₃ | 6-methyl-3,4-dihydro-2H-pyran-2-yl |
| F | H | 3,6-dihydro-2H-thiopyran-4-yl |
| F | CH₃ | 3,6-dihydro-2H-thiopyran-4-yl |
| F | H | 3,6-dihydro-2H-thiopyran-5-yl |
| F | CH₃ | 3,6-dihydro-2H-thiopyran-5-yl |
| F | H | 3,4-dihydro-2H-thiopyran-4-yl |
| F | CH₃ | 3,4-dihydro-2H-thiopyran-4-yl |
| F | H | 3,4-dihydro-2H-thiopyran-5-yl |
| F | CH₃ | 3,4-dihydro-2H-thiopyran-5-yl |
| F | H | 3,4-dihydro-2H-thiopyran-6-yl |
| F | CH₃ | 3,4-dihydro-2H-thiopyran-6-yl |
| F | H | 2,2,6,6-tetramethyl-3,6-dihydro-2H-thiopyran-4-yl |
| F | CH₃ | 2,2,6,6-tetramethyl-3,6-dihydro-2H-thiopyran-4-yl |

The N-phenyltetrahydroindazole derivatives Ia and Ib, and herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts or aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient.

Examples of formulations are as follows:

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 1.004 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.006 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.001 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.002 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.005 is intimately mixed with 97 parts by weight of particulate kaolin. A dust is obtained containing 3% by weight of the active ingredient.

VII. 30 parts by weight of compound no. 1.003 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.004 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3.0, preferably 0.01 to 0.5, kg of active ingredient per hectare.

In view of the number of application methods possible, the compounds according to the invention, or agents containing them, may be used in a further large number of crops for removing unwanted plants. The following crops may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. aitissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | tea plants |
| Camellia sinensis | |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum. Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the N-phenyltetrahydroindazoles of the formula Ia and Ib may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, quinolinecarboxylic acids, phenyloxy- and heteroaryloxypropionic acids and salts, esters and amides thereof, etc.

It may also be useful to apply the N-phenyltetrahydroindazoles of the formula Ia and Ib, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below may be used, after appropriate modifications of the starting materials, to obtain further compounds of the formula Ia and Ib. The compounds obtained are listed with their physical data in the tables below; compounds without these data may be prepared from the appropriate materials in analogous manner. In view of their close structural relationship to the compounds which have been manufactured and investigated, they are expected to have a similar action.

EXAMPLE 1

Preparation of 3-chloro-2-[4-chloro-2-fluoro-5-(5,6-dihydro-2H-pyran-3-ylmethoxy)phenyl]-4,5,6,7-tetrahydroindazole

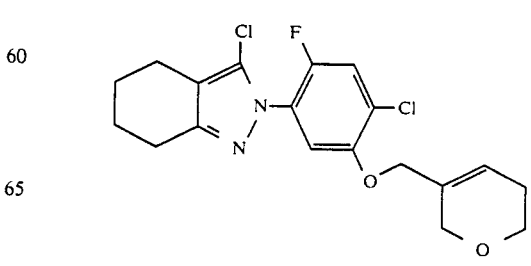

2.1 g (16 mmol) of 3-chloromethyl-5,6dihydro-2H-pyran were added at 25° C. to a mixture of 4.5 g (15 mmol) of 3-chloro-2-(4-chloro-2fluoro-5-hydroxyphenyl)-4,5,6,7-tetrahydroindazole, 2.5 g (18 mmol) of potassium carbonate and 0.5 g (3 mmol) of sodium iodide in 50 ml of dimethylformamide, and the reaction mixture was stirred for 12 hours. 100 ml of water were added, and the precipitate was isolated, washed with water and dried, resulting in 5 g (84%) of the title compound [melting point 90° to 92° C.]. Compound No. 1.002.

EXAMPLE 2

Preparation of 3-chloro-2-[4-chloro2-fluoro-5-(3-hexahydrothiopyranylmethoxy)phenyl]-4,5,6,7-tetrahydroindazole

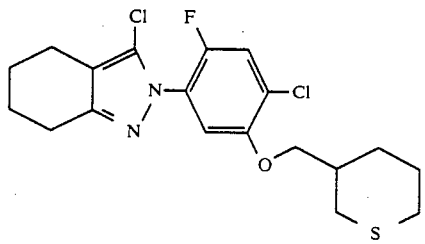

(a) 47.9 g (250 mmol) of 2-chloro-4-fluoro-5-nitrophenol, 34.6 g (250 mmol) of potassium carbonate, 1 g of potassium iodide and 58.5 g (300 mmol) of 3-bromomethyltetrahydrothiopyran in 500 ml of acetonitrile were refluxed for 5 hours. The mixture was cooled to 25° C. and filtered, the solvent was removed from the filtrate, the residue was taken up in methylene chloride, and the solution was washed with water, dried and concentrated. 22 g (29%) of 2-chloro5-fluoro-5-nitro-1-(3-tetrahydrothiopyranylmethoxy)benzene (melting point 100° to 103° C.) were obtained.

(b) A suspension of 26 g (85 mmol) of the above nitro compound was added to a mixture of 14.3 g (260 mmol) of iron powder in 100 ml of methanol and 28 ml of glacial acetic acid at the boiling point, and the mixture was refluxed for a further 2 hours. The reaction mixture was cooled to 25° C. and then poured into water, the mixture was extracted with ethyl acetate, and the extracts were dried and concentrated. Purification resulted in 15.5 g (66%) of 4-chloro-2-fluoro-5-(3-tetrahydrothiopyranylmethoxy)aniline (melting point 66° to 68° C.).

(c) 100 ml of 10% strength hydrochloric acid were added to a solution of 13.8 g (50 mmol) of 4-chloro-2-fluoro-5-(3tetrahydrothiopyranylmethoxy)aniline in 50 ml of glacial acetic acid and then, at −5° to 0° C., 3.5 g (50 mmol) of sodium nitrite in 20 ml of water were added within 15 min.

The solution obtained after stirring at this temperature for 1 hour was added dropwise, at −10° to −5° C., to 28.2 g (125 mmol) of tin(II) chloride dihydrate in 30 ml of concentrated hydrochloric acid, and the mixture was stirred at 0° C. for a further 2 hours. While cooling in ice, the mixture was made alkaline with concentrated sodium hydroxide solution and was extracted with methylene chloride, the organic phases were dried and concentrated, and the residue was stirred with petroleum ether. 12 g (82%) of 4-chloro-2-fluoro-5-(3-tetrahydrothiopyranylmethoxy)phenylhydrazine (melting point 83° to 87° C.) were obtained.

(d) 7.3 g (25 mmol) of the phenylhydrazine obtained in this way were added to 4.3 g (25 mmol) of ethyl cyclohexanone-2carboxylate in 100 ml of glacial acetic acid, and the mixture was refluxed for 5 hours. It was cooled to 25° C. and then concentrated, precipitation was carried out by adding a little water/petroleum ether, and the residue was dried. 9 g (90%) of 2-[4-chloro-2-fluoro-5-(3-tetrahydrothiopyranylmethoxy)-phenyl]-1,2,4,5,6,7-hexahydro-3H-indazol-3-one (melting point 96° to 100° C.) were obtained.

(e) 8.7 g (22mmol) of the above 3-indazolone were added to a solution of 30 ml of trichloromethyl chloroformate in 500 ml of toluene and the mixture was slowly heated. After cooling to 25° C. it was flushed with nitrogen, concentrated and purified as usual. 2 g (22%) of the title compound were obtained as an oil (compound No. 1.005).

USE EXAMPLES

The action of the N-phenyltetrahydroindazole derivatives Ia and Ib on the growth of test plants is demonstrated in the following greenhouse experiments.

The vessels employed were plastic flowerpots having a volume of 300 cm³ and filled with a sandy loam containing about 3.0% humus. The seeds of the test plants were sown separately, according to species.

For the postemergence treatment, either plants sown directly in the pots and grown there were used, or plants which were cultivated separately as seedling and were transplanted to the vessels a few days before treatment.

Depending on growth form, the plants were grown to a height of 3 to 15 cm before being treated with the active ingredients, which were suspended or emulsified in water and sprayed through finely distributing nozzles. The application rate for postemergence treatment was 0.03 kg/ha.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatment assessed.

The assessment scale was 0 to 100, 100 denoting nonemergence or complete destruction of at least the visible plant parts, and 0 denoting no damage or normal growth.

The plants used in the greenhouse experiments were *Abutilon theophrasti, Amaranthus retroflexus, Chenopodium album, Chrysanthemum corinarium, Galium aparine, Ipomoea spp., Lamium amplexicaule, Malva neglecta, Solanum nigrum* and *Stellaria media.*

Compounds 1.005, 1.003, 1.001 and 1.002, applied postemergence at a rate of 0.03 kg/ha, provide excellent control of unwanted broadleaved plants.

TABLE 1

Structure Ia: 4,5,6,7-tetrahydro-2H-indazole with 3-Cl, N-substituted with phenyl bearing F, R¹, and OCH(R')(R'')

| Compound No. | R¹ | R' | R'' | Physical data: [mp (°C); IR (cm$^{-1}$); $^1$H-NMR (ppm)] |
|---|---|---|---|---|
| 1.001 | Cl | H | tetrahydropyran-4-yl (O in ring) | NMR: 7.0(d), 7.35(d) |
| 1.002 | Cl | H | 3,6-dihydro-2H-pyran-4-yl | mp: 90–92 |
| 1.003 | Cl | H | tetrahydropyran-4-yl | IR: 2935, 1505, 1448, 1393, 1197 |
| 1.004 | Cl | H | 3,6-dihydro-2H-thiopyran-4-yl | mp: 113–115 |
| 1.005 | Cl | H | tetrahydrothiopyran-3-yl | IR: 2926, 1504, 1466, 1393, 1197 |
| 1.006 | Cl | H | CH=C(CH$_3$)CO$_2$CH$_2$CH$_3$ | mp: 93–95 |
| 1.007 | Cl | H | tetrahydrofuran-3-yl | IR: 2935, 1505, 1393, 1197 |
| 1.008 | Cl | H | tetrahydrofuran-2-yl (2-methyl) | mp: 70–71 |
| 1.009 | Cl | H | tetrahydropyran-2-yl | IR: 2936, 1504, 1198, 1049 |

TABLE 2

Structure Ib: 4,5,6,7-tetrahydro-2H-indazole with 3-Cl, N-substituted with phenyl bearing OR³ and R¹

| Compound No. | R¹ | R³ | Physical data: [mp (°C); IR (cm$^{-1}$); $^1$H-NMR (ppm)] |
|---|---|---|---|
| 2.001 | Cl | CH$_2$CH=C(CH$_3$)CO$_2$CH$_3$ | mp: 82–85 |
| 2.002 | Cl | CH$_2$CH=C(CH$_3$)CO$_2$CH$_2$CH$_3$ | mp: 75–76 |
| 2.003 | Cl | CH$_2$CH$_3$ | mp: 63–65 |
| 2.004 | Cl | CH$_2$CH=CH$_2$ | mp: 74–76 |
| 2.005 | Cl | CH$_2$C≡CH | mp: 99–100 |
| 2.006 | Cl | CH(CH$_3$)$_2$ | IR: 2936, 1594, 1492, 1060 |
| 2.007 | Cl | CH(CH$_3$)C≡CH | mp: 65–67 |
| 2.008 | Cl | (CH$_2$)$_4$CH(CH$_3$)$_2$ | IR: 2936, 1595, 1494, 1063 |
| 2.009 | Cl | CH$_2$C(CH$_3$)$_3$ | IR: 2954, 2936, 1594, 1494, 1400, 1064 |
| 2.010 | Cl | (CH$_2$)$_5$CH$_3$ | mp: 45–47 |

TABLE 3

Structure Ib: 4,5,6,7-tetrahydro-2H-indazole with 3-Cl, N-substituted with phenyl bearing OCH(R')(R'') and R¹

| Compound No. | R¹ | R' | R'' | Physical data: [mp (°C); IR (cm$^{-1}$); $^1$H-NMR (ppm)] |
|---|---|---|---|---|
| 3.001 | Cl | H | tetrahydropyran-4-yl | mp: 62–65 |
| 3.002 | Cl | H | 3,6-dihydro-2H-pyran-4-yl | mp: 63–65 |
| 3.003 | Cl | H | tetrahydropyran-4-yl | IR: 2935, 1593, 1494, 1094, 1063 |
| 3.004 | Cl | H | 3,6-dihydro-2H-thiopyran-4-yl | IR: 2935, 1593, 1493, 1061 |
| 3.005 | Cl | H | tetrahydrothiopyran-3-yl | mp: 103–105 |
| 3.006 | Cl | H | 2,2,6,6-tetramethyl-dihydrothiopyranyl (with CH$_3$ groups) | IR: 2934, 1592, 1365, 1220, 1059 |

TABLE 3-continued

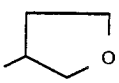

| Compound No. | R¹ | R' | R" | Physical data: [mp (°C.); IR (cm⁻¹); ¹H-NMR (ppm)] |
|---|---|---|---|---|
| 3.007 | Cl | H | (tetrahydrofuran-3-yl methyl) | IR: 2936, 1592, 1493, 1063 |
| 3.008 | Cl | H | (tetrahydrofuran-2-yl methyl) | IR: 2935, 1593, 1494, 1063 |
| 3.009 | Cl | H | (tetrahydropyran-2-yl methyl) | IR: 2935, 1593, 1494, 1095, 1063 |
| 3.010 | Cl | H | H₃C-(tetrahydropyranyl) | IR: 2934, 1593, 1494, 1063 |

We claim:

1. An N-(Phenyl)-tetrahydroindazole of the formula Ia or Ib

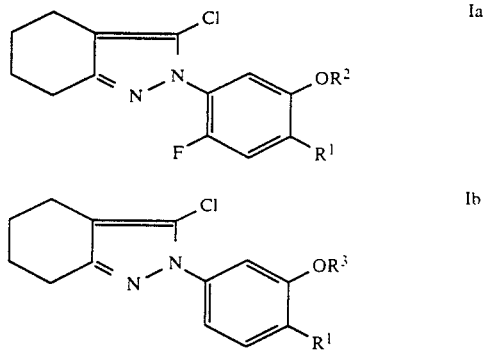

wherein
R¹ is halogen;
R² is $C_1$–$C_3$-alkyl which is substituted in the 1-or 2-position by a 5- or 6-membered saturated or monounsaturated heterocycle which contains one oxygen heteroatom and can be substituted by from one to four $C_1$–$C_4$-alkyls, and
R³ is $C_1$–$C_3$-alkyl which is substituted in the 1- or 2-position by a 5-or 6-membered saturated or monounsaturated heterocycle which contains one oxygen as heteroatom and can be substituted by from one to four $C_1$–$C_4$-alkyls.

2. An N-(phenyl)-tetrahydroindazole of the formula Ia as set forth in claim 1, wherein R¹ is Cl and R² is CH₂ which is substituted by a tetrahydropyranyl group.

3. A herbicidal composition which comprises an effective amount of an N-(phenyl)-tetrahydroindazole of the formula Ia and/or Ib as set forth in claim 1, and inert additives.

4. A process for combating the growth of unwanted plants, wherein the unwanted plants and/or their habitat are treated with a herbicidally effective amount of an N-(phenyl)-tetrahydroindazole Ia and/or Ib as set forth in claim 1.

5. A process for combating the growth of unwanted plants and/or their habitat are treated with a herbicidally effective amount the N-(phenyl)-tetrahydroindazole of claim 2.

* * * * *